(12) United States Patent
Johansson et al.

(10) Patent No.: US 8,106,208 B2
(45) Date of Patent: Jan. 31, 2012

(54) BENZAMIDE COMPOUNDS THAT ACT AS NK RECEPTOR ANTAGONISTS

(75) Inventors: Anders Johansson, Mölndal (SE); Johan Johansson, Mölndal (SE); Carl-Gustav Sigfridsson, Mölndal (SE)

(73) Assignee: Albireo AB, Gothenburg (SE)

( * ) Notice: Subject to any disclaimer, the term of this patent is extended or adjusted under 35 U.S.C. 154(b) by 380 days.

(21) Appl. No.: 11/747,322

(22) Filed: May 11, 2007

(65) Prior Publication Data

US 2007/0270398 A1    Nov. 22, 2007

Related U.S. Application Data

(60) Provisional application No. 60/801,577, filed on May 18, 2006.

(51) Int. Cl.
    *C07D 401/04* (2006.01)
    *A61K 31/454* (2006.01)
(52) U.S. Cl. ........................ 546/208; 514/326
(58) Field of Classification Search .................. 546/208; 514/210.01, 326
    See application file for complete search history.

(56) References Cited

U.S. PATENT DOCUMENTS 7,402,581 B2 * 7/2008 Johansson et al. ......... 514/235.5

FOREIGN PATENT DOCUMENTS

| EP | 0 625 509 B1 | 7/1997 |
|---|---|---|
| EP | 0 630 887 B1 | 7/1999 |
| EP | 0 790 248 B1 | 5/2003 |
| EP | 0 791 592 B1 | 5/2003 |
| EP | 0 962 457 B1 | 8/2003 |
| WO | WO 95/05377 | 2/1995 |
| WO | WO 95/12577 | 5/1995 |
| WO | WO 95/15961 | 6/1995 |
| WO | WO 96/05193 | 2/1996 |
| WO | WO 96/24582 | 8/1996 |
| WO | WO 97/25322 | 7/1997 |
| WO | WO 97/27185 | 7/1997 |
| WO | WO 99/01451 | 1/1999 |
| WO | WO 00/02859 | 1/2000 |
| WO | WO 00/20003 | 4/2000 |
| WO | WO 00/20389 | 4/2000 |
| WO | WO 00/25766 | 5/2000 |
| WO | WO 00/34243 | 6/2000 |
| WO | WO 02/051807 A1 | 7/2002 |
| WO | WO 03/037889 A1 | 5/2003 |
| WO | WO 2004/110344 A2 | 12/2004 |

OTHER PUBLICATIONS

Burkholder et. al. "Synthesis and Structure—Activity Relationships for a Series of Substituted Pyrrolidine NK1/NK2 Receptor Antagonists" Bioorganic & Medicinal Chemistry Letters, vol. 7, No. 19, pp. 2531-2536.*

Ting et. al. "Synthesis of Substituted 4(Z)-(Methoxyimino)pentyl-1-piperidines as Dual NK1/NK2 Inhibitors" Biorganic and Medicinal Chemistry Letters 2001, 11, 491-494.*

Vandenberg, et al., "Herg $K^+$ channels: friend and foe," Trends in Pharmacological Sciences, vol. 22, No. 5, pp. 240-246, 2001.

MacKenzie, et al., "4-Amino-2-(aryl)-butylbenzamides and Their Conformationally Constrained Analogues. Potent Antagonists of the Human Neurokinin-2 ($NK_2$) Receptor," Bioorganic & Medicinal Chemistry Letters, vol. 13, pp. 2211-2215, 2003.

\* cited by examiner

*Primary Examiner* — David K O Dell
(74) *Attorney, Agent, or Firm* — Fish & Richardson P.C.

(57) ABSTRACT

The present invention relates to new compounds of formula I, to pharmaceutical compositions comprising said compounds, and to the use of said compounds in therapy. The present invention further relates to processes for the preparation of compounds of formula I.

3 Claims, No Drawings

BENZAMIDE COMPOUNDS THAT ACT AS NK RECEPTOR ANTAGONISTS

This application claims the priority benefit of U.S. Provisional Application Ser. No. 60/801,577, filed on May 18, 2006.

FIELD OF THE INVENTION

The present invention relates to new compounds of formula I, to pharmaceutical compositions comprising said compounds, and to the use of said compounds in therapy. The present invention further relates to processes for the preparation of compounds of formula I.

BACKGROUND OF THE INVENTION

The neurokinins, also known as the tachykinins, comprise a class of peptide neurotransmitters which are found in the peripheral and central nervous systems. The three principal tachykinins are Substance P (SP), Neurokinin A (NKA) and Neurokinin B (NKB). At least three receptor types are known for the three principal tachykinins. Based upon their relative selectivities favoring the agonists SP, NKA and NKB, the receptors are classified as neurokinin 1 ($NK_1$), neurokinin 2 ($NK_2$) and neurokinin 3 ($NK_3$) receptors, respectively.

There is a need for an orally active NK receptor antagonist for the treatment of e.g. respiratory, cardiovascular, neuro, pain, oncology, inflammatory and/or gastrointestinal disorders. In order to increase the therapeutic index of such therapy it is desirable to obtain such a compound possessing no or minimal toxicity as well as being selective to said NK receptors. Furthermore, it is considered necessary that said medicament has favourable pharmacokinetic and metabolic properties thus providing an improved therapeutic and safety profile such as lower liver enzyme inhibiting properties.

It is well known that certain compounds may cause undesirable effects on cardiac repolarisation in man, observed as a prolongation of the QT interval on electrocardiograms (ECG). In extreme circumstances, this drug-induced prolongation of the QT interval can lead to a type of cardiac arrhythmia called Torsades de Pointes (TdP; Vandenberg et al. hERG $K^+$ channels: friend and foe. Trends Pharmacol Sci 2001; 22: 240-246), leading ultimately to ventricular fibrillation and sudden death. The primary event in this syndrome is inhibition of the rapid component of the delayed rectifying potassium current (IKr) by these compounds. The compounds bind to the aperture-forming alpha sub-units of the channel protein carrying this current. The aperture-forming alpha sub-units are encoded by the human ether-a-go-go-related gene (hERG). Since IKr plays a key role in repolarisation of the cardiac action potential, its inhibition slows repolarisation and this is manifested as a prolongation of the QT interval. Whilst QT interval prolongation is not a safety concern per se, it carries a risk of cardiovascular adverse effects and in a small percentage of people it can lead to TdP and degeneration into ventricular fibrillation.

In particular, it is desirable that the NK receptor antagonist has a suitable balance of pharmacodynamic and pharmacokinetic properties to make it therapeutically useful. In addition to having sufficient and selective potency, the NK receptor antagonist needs to be balanced with regard to relevant pharmacokinetic properties. Thus, it is necessary that the NK antagonist has: a) sufficiently high affinities at the different NK receptors, b) pharmacokinetic properties (absorption, distribution and elimination properties) that makes it possible for the drug to act at the targeted NK receptors mainly in the periphery. For instance, the NK receptor antagonist needs to have sufficiently high metabolic stability, c) sufficiently low affinities to different ion channels, such as the hERG-encoded potassium channel in order to obtain a tolerable safety profile and d) liver enzyme (such as CYP3A4) inhibiting properties at a low level to prevent drug-drug interactions.

Furthermore, in order to enhance the efficacy of the NK receptor antagonist, it is beneficial to have an NK antagonist with a long-lasting competitive mode of action at the receptor.

EP 0625509, EP 0630887, WO 95/05377, WO 95/12577, WO 95/15961, WO 96/24582, WO 00/02859, WO 00/20003, WO 00/20389, WO 00/25766, WO 00/34243, WO 02/51807 and WO 03/037889 disclose piperidinylbutylamide derivatives, which are tachykinin antagonists.

"4-Amino-2-(aryl)-butylbenzamides and Their Conformationally Constrained Analogues. Potent Antagonists of the Human Neurokinin-2 ($NK_2$) Receptor", Roderick MacKenzie, A., et al, *Bioorganic & Medicinal Chemistry Letters* (2003), 13, 2211-2215, discloses the compound N-[2-(3,4-dichlorophenyl)-4-(3-morpholin-4-ylazetidin-1-yl)butyl]-N-methylbenzamide which was found to possess functional $NK_2$ receptor antagonistic properties.

WO 96/05193, WO 97/27185 and EP 0962457 disclose azetidinylalkyllactam derivatives with tachykinin antagonist activity.

EP 0790248 discloses azetidinylalkylazapiperidones and azetidinylalkyloxapiperidones, which are stated to be tachykinin antagonists.

WO 99/01451 and WO 97/25322 disclose azetidinylalkylpiperidine derivatives claimed to be tachykinin antagonists.

EP 0791592 discloses azetidinylalkylglutarimides with tachykinin antagonistic properties.

WO2004/110344 A2 discloses dual NK1,2 antagonists and the use thereof.

An object of the present invention was to provide novel neurokinin antagonists useful in therapy. A further object was to provide novel compounds having well-balanced pharmacokinetic and pharmacodynamic properties.

OUTLINE OF THE INVENTION

The present invention provides a compound of the general formula (I)

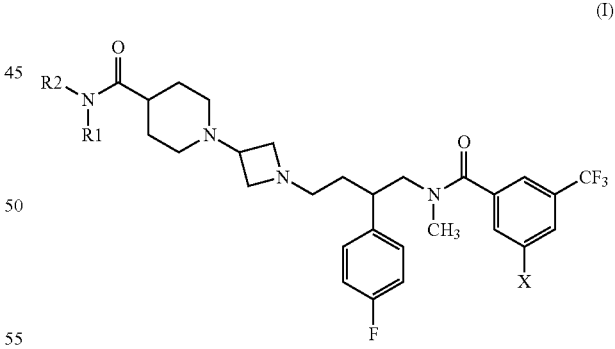

wherein
R1 and R2 is each and independently selected from hydrogen, methyl, ethyl or R1 and R2 form a four, five or six membered ring together with the amide nitrogen, said ring optionally containing an oxygen atom;
X is bromo or chloro;
as well as pharmaceutically and pharmacologically acceptable salts thereof, and enantiomers of the compound of formula I and salts thereof.

In one embodiment, R1 and R2, together with the amide nitrogen, form a morpholine ring.

In one embodiment, R1 and R2, together with the amide nitrogen, form an azetidine ring.

In one embodiment, R1 and R2, together with the amide nitrogen, form a pyrrolidine ring.

In one embodiment, R1 and R2, together with the amide nitrogen, form an isoxazolidine ring.

In one embodiment, R1 and R2, together with the amide nitrogen, form an oxazolidine ring.

The present invention relates to compounds of formula I as defined above as well as to salts thereof. Salts for use in pharmaceutical compositions will be pharmaceutically acceptable salts, but other salts may be useful in the production of the compounds of formula I.

The compounds of the present invention are capable of forming salts with various inorganic and organic acids and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, palmoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate.

Pharmaceutically acceptable salts may be prepared from the corresponding acid in conventional manner. Non-pharmaceutically-acceptable salts may be useful as intermediates and as such are another aspect of the present invention.

Acid addition salts may also be in the form of polymeric salts such as polymeric sulfonates.

The salts may be formed by conventional means, such as by reacting the free base form of the product with one or more equivalents of the appropriate acid in a solvent or medium in which the salt is poorly soluble, or in a solvent such as water, which is removed in vacuo or by freeze drying or by exchanging the anions of an existing salt for another anion on a suitable ion-exchange resin.

Compounds of formula I have one chiral center, and it is to be understood that the invention encompasses all optical isomers and enantiomers. The compounds according to formula (I) can be in the form of the single stereoisomers, i.e. the single enantiomer (the R-enantiomer or the S-enantiomer). The compounds according to formula (I) can also be in the form of a racemic mixture, i.e. an equimolar mixture of enantiomers.

The compounds can exist as a mixture of conformational isomers. The compounds of this invention comprise both mixtures of, and individual, conformational isomers.

Pharmaceutical Formulations

According to one aspect of the present invention there is provided a pharmaceutical formulation comprising a compound of formula I, as a single enantiomer, a racemate or a mixture thereof as a free base or pharmaceutically acceptable salts thereof, for use in prevention and/or treatment of respiratory, cardiovascular, neuro, pain, oncology, inflammatory and/or gastrointestinal disorders.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, pellets, capsules, aqueous or oily solutions, suspensions, emulsions, creams, ointments, gels, nasal sprays, suppositories, finely divided powders or aerosols or nebulizers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans in a daily dose of a compound of formula I of from 0.01 to 25 mg/kg body weight. Alternatively, a daily dose of the compound of formula I from 0.1 to 5 mg/kg body weight is administered. This daily dose may be given in divided doses as necessary, the precise amount of the compound administered and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of from 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Medical and Pharmaceutical Use

The present invention provides a method of treating or preventing a disease condition wherein antagonism of tachykinins acting at the NK receptors is beneficial which comprises administering to a subject an effective amount of a compound of the formula (I) or a pharmaceutically-acceptable salt thereof. The present invention also provides the use of a compound of the formula (I) or a pharmaceutically acceptable salt thereof in the preparation of a medicament for use in a disease condition wherein antagonism of tachykinins acting at the NK receptors is beneficial.

The compounds of formula (I) or pharmaceutically acceptable salts or solvates thereof may be used in the manufacture of a medicament for use in the prevention or treatment of respiratory, cardiovascular, neuro, pain, oncology and/or gastrointestinal disorders.

Examples of such disorders are asthma, allergic rhinitis, pulmonary diseases, cough, cold, inflammation, chronic obstructive pulmonary disease, airway reactivity, urticaria, hypertension, rheumatoid arthritis, edema, angiogenesis, pain, migraine, tension headache, psychoses, depression, anxiety, Alzheimer's disease, schizophrenia, Huntington's disease, bladder hypermotility, urinary incontinence, eating disorder, manic depression, substance dependence, movement disorder, cognitive disorder, obesity, stress disorders, micturition disorders, mania, hypomania and aggression, bipolar disorder, cancer, carcinoma, fibromyalgia, non cardiac chest pain, gastrointestinal hypermotility, gastric asthma, Crohn's disease, gastric emptying disorders, ulcerative colitis, irritable bowel syndrome (IBS), inflammatory bowel disease (IBD), emesis, gastric asthma, gastric motility disorders, gastro-esophageal reflux disease (GERD) or functional dyspepsia.

Methods of Preparation

In another aspect the present invention provides a process for preparing a compound of the formula (I) or salts thereof which process comprises:

a) reacting a compound of the formula (II) with a compound of the formula (III):

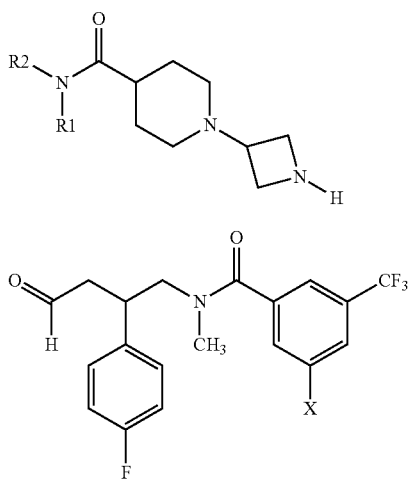

(II)

(III)

wherein R1, R2 and X are as hereinbefore defined; and the conditions are such that reductive alkylation of the compound of the formula (II) forms an N—C bond between the nitrogen atom of the azetidine group of the compound of formula (II) and the carbon atom of the aldehyde group of the compounds of formula (III); or b) reacting a compound of the formula (II) with a compound of the formula (IV):

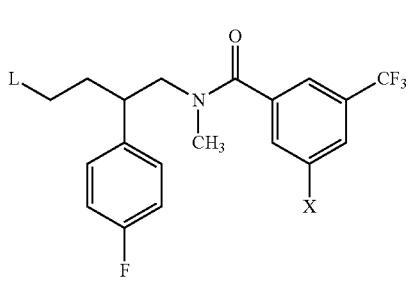

(IV)

wherein X is as hereinbefore defined; and L is a group such that alkylation of the compound of the formula (II) forms an N—C bond between the nitrogen atom of the azetidine group of the compound of formula (II) and the carbon atom of the compounds of formula (IV) that is adjacent to the L group; or c) reacting a compound of the formula (V) with a compound of the formula (VI):

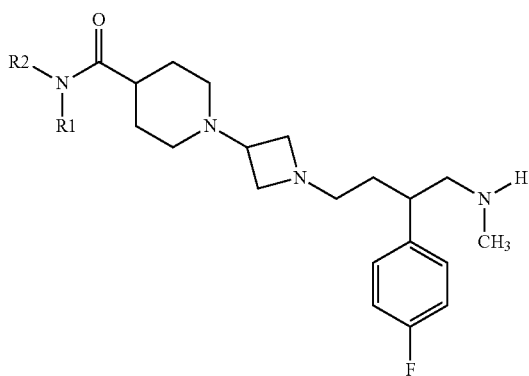

(V)

(VI)

wherein R1, R2 and X are as hereinbefore defined; and L' is a leaving group;

and optionally forming a pharmaceutically acceptable salt.

The compounds of the formulae (II) and (III) are reacted under conditions of reductive alkylation. The reaction is typically performed at a non-extreme temperature, for example 0-10° C., in a substantially inert solvent for example dichloromethane. Typical reducing agents include borohydrides such as sodium cyanoborohydride.

The compounds of the formulae (II) and (IV) are reacted under conditions of alkylation. Typically in the compounds of the formula (IV) L is a leaving group such as halogen or alkylsulfonyloxy. The reaction is typically performed at an elevated temperature, for example 30-130° C., in a substantially inert solvent for example DMF.

The compounds of the formula (II) may be prepared in conventional manner, for example by reacting a compound of the formula VII:

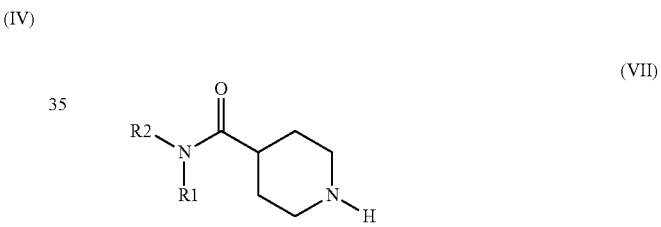

(VII)

with a compound of the formula (VIII):

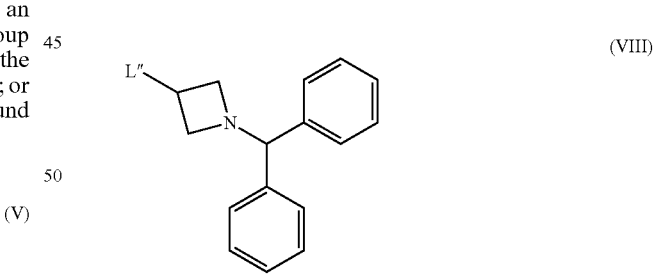

(VIII)

wherein R1 and R2 and are as hereinbefore defined; and L" is a group such that alkylation of the compound of the formula (VII) forms an N—C bond between the nitrogen atom of the piperidine group of the compound of formula (VII) and the carbon atom of the compounds of formula (VIII) that is adjacent to the L" group; and subsequently removing the protective group (—CH(Ph)$_2$) as for instance by a catalytic hydrogenation reaction.

The compounds of the formula (III) may be prepared, for example, by reacting a compound of the formula (IX) with a compound of the formula (VI):

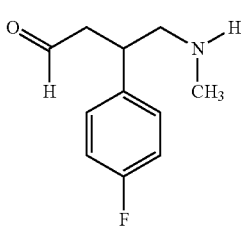

(IX)

wherein R1 is as hereinbefore defined under conventional acylation conditions.

The compounds of the formula (IV) may be prepared, for example, by reacting a compound of the formula (VI) with a compound of the formula (X):

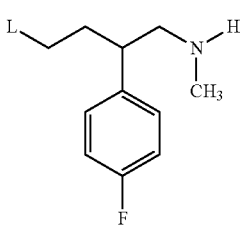

(X)

wherein L is as hereinbefore defined under conventional acylation conditions.

The compounds of the formulae (V) and (VI) may be reacted under conventional acylation conditions wherein

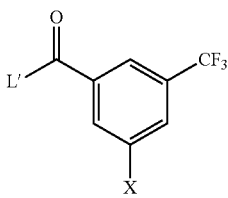

is an acid or an activated acid derivative. Such activated acid derivatives are well known in the literature. They may be formed in situ from the acid or they may be prepared, isolated and subsequently reacted. Typically L' is chloro thereby forming the acid chloride. Typically the acylation reaction is performed in the presence of a non-nucleophilic base, for example N,N-diisopropylethylamine, in a substantially inert solvent such as dichloromethane at a non-extreme temperature.

The compounds of the formula (VII) and (VIII) are known or may be prepared in conventional manner.

EXAMPLES

It should be emphasised that the compounds of the present invention most often show highly complex NMR spectra due to the existence of conformational isomers. This is believed to be a result from slow rotation about the amide and/or aryl bond. The following abbreviations are used in the presentation of the NMR data of the compounds: s—singlet; d—doublet; t—triplet; qt—quartet; qn—quintet; m—multiplet; b—broad; cm—complex multiplet, which may include broad peaks.

The following examples will describe, but not limit, the invention.

The following abbreviations are used in the experimental: DIPEA (N,N-diisopropylethylamine), TBTU (N,N,N',N'-tetramethyl-O-(benzotriazol-1-yl)uronium tetrafluoroborate), DMF (N,N-dimethylformamide), THF (tetrahydrofuran) and RT (room temperature).

Example 1

N-[(2S)-4-{3-[4-(Azetidin-1-ylcarbonyl)piperidin-1-yl]azetidin-1-yl}-2-(4-fluorophenyl)butyl]-3-bromo-N-methyl-5-(trifluoromethyl)benzamide

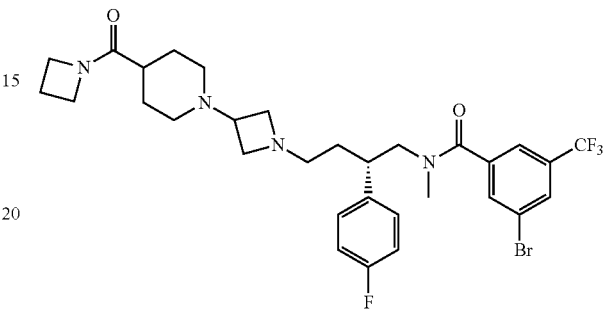

3-Bromo-N-[(2S)-2-(4-fluorophenyl)-4-oxobutyl]-N-methyl-5-(trifluoromethyl)benzamide (see method 1; 0.16 g, 0.36 mmol) and 1-azetidin-3-yl-4-(azetidin-1-ylcarbonyl)piperidine (see method 2; 0.10 g, 0.47 mmol) were dissolved in methylene chloride (10 mL) together with a small amount of dry methanol (0.2 mL). To the resultant solution were added DIPEA (0.14 g, 1.08 mmol) and sodium triacetoxyborohydride (0.15 g, 0.72 mmol). The mixture was stirred under nitrogen for 4 h at RT. The mixture was diluted with methylene chloride and washed twice with saturated aqueous NaHCO$_3$ and then with brine. The organic phase was filtered through a phase separator and the solvent was removed by evaporation. The product was purified by chromatography on silica gel (methanol-methylene chloride, 10:1). There was obtained 0.14 g (59%) of the title compound as a white foam. $^1$H NMR (500 MHz, CDCl$_3$): δ 1.4-1.8 (cm, 6H), 2.1 (m, 1H) 2.2 (qn, 2H), 2.3-2.4 (cm, 2H), 2.5-3.5 (cm, 14H), 3.6 (d, 1H), 3.9 (t, 2H), 4.1 (t, 2H), 6.8-7.4 (cm, 6H), 7.7 (s, 1H); LCMS: m/z 654 (M+1)$^+$.

Example 2

1-{1-[(3S)-4-[[3-Bromo-5-(trifluoromethyl)benzoyl](methyl)amino]-3-(4-fluorophenyl)butyl]azetidin-3-yl}-N,N-dimethylpiperidine-4-carboxamide diformate

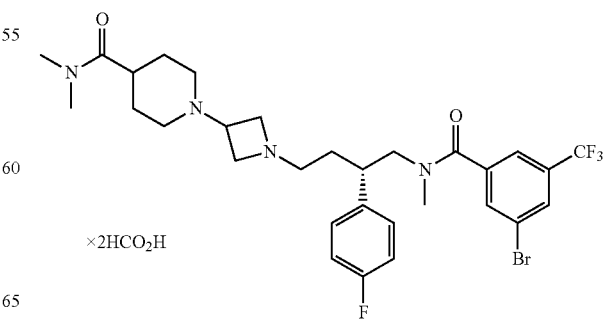

A mixture of 3-bromo-N-[(2S)-2-(4-fluorophenyl)-4-oxobutyl]-N-methyl-5-(trifluoromethyl)benzamide (see method 1; 0.178 g, 0.40 mmol), 1-azetidin-3-yl-N,N-dimethylpiperidine-4-carboxamide (see method 3; 0.084 g, 0.40 mmol), acetic acid (0.3 mL), (polystyrylmethyl)trimethylammonium cyanoborohydride (0.098 g, 0.52 mmol) and methanol was stirred at RT for 6 h. The resin was filtered off and washed with methanol. The solvent of the filtrate was removed by evaporation and the product was purified by reversed phase chromatography (C8) using acetonitrile and aqueous ammonium formate/formic acid solution (0.1 M $N_4CO_2H$, 0.1 M $HCO_2H$, pH 4) as eluent. There was obtained 0.23 g (77%) of the title compound. $^1H$ NMR (500 MHz, $CD_3OD$): δ 1.6-2.0 (cm, 6H), 2.6-4.2 (cm, 24H), 7.0-8.0 (cm, 6H), 8.4 (s, 1H); LCMS: m/z 642 $(M+1)^+$.

Example 3

1-{1-[(3S)-4-[[3-Bromo-5-(trifluoromethyl)benzoyl](methyl)amino]-3-(4-fluorophenyl)butyl]azetidin-3-yl}piperidine-4-carboxamide

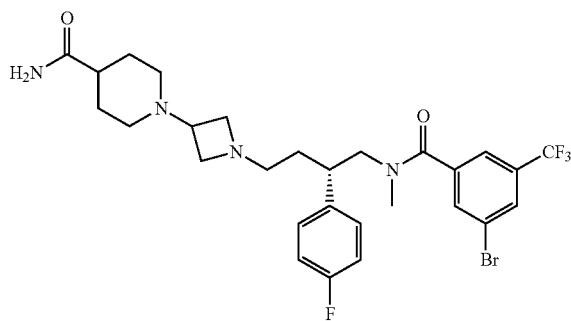

3-Bromo-N-[(2S)-2-(4-fluorophenyl)-4-oxobutyl]-N-methyl-5-(trifluoromethyl)benzamide (see method 1; 1.00 g, 2.24 mmol) and 1-azetidin-3-ylpiperidine-4-carboxamide (see method 4; 0.49 g, 2.69 mmol) and triethylamine (1.24 mL, 9.0 mmol) were dissolved in methylene chloride (30 mL) together with methanol (5 mL). To the resultant solution was added sodium cyanoborohydride (0.21 g, 3.36 mmol) and the mixture was stirred at RT for 20 min. The solvent was removed by evaporation and the residue was partitioned between methylene chloride and saturated aqueous $NaHCO_3$. The organic phase was filtered through a phase separator and the solvent was removed by evaporation. The product was purified by chromatography on silica gel (ammonia saturated methanol/methylene chloride, 1-20% methanol). There was obtained 0.24 g (17%) of the title compound. $^1H$ NMR (500 MHz, $CDCl_3$): δ 1.4-3.8 (cm, 23H), 5.7 (b, 1H), 5.8 (b, 1H), 6.8-7.4 (cm, 6H), 7.7 (s, 1H); LCMS: m/z 614 $(M+1)^+$.

Example 3a

In order to obtain additional information regarding existing solid form suspension crystallisation was carried out at room temperature in different solvents. After approx. 2 weeks the solid form was checked with XRPD. Samples slurried in methanol, ethanol, i-propanol, aceton and chloroform display very similar patterns in XRPD, which differ from that of the original sample. The crystallinity is notably better for the new form. The material suspended in ethyl methyl ketone displays a completely unique pattern. Hot-stage XRPD performed on the sample suspended in i-propanol show that the X-ray powder pattern is changed above 120° C. The new pattern is also different from that of the original sample.

Maleate salt of 1-{1-[(3S)-4-[[3-Bromo-5-(trifluoromethyl)benzoyl](methyl)amino]-3-(4-fluorophenyl)butyl]azetidin-3-yl}piperidine-4-carboxamide 1-{1-[(3S)-4-[[3-Bromo-5-(trifluoromethyl)benzoyl](methyl)amino]-3-(4-fluorophenyl)butyl]azetidin-3-yl}piperidine-4-carboxamide (2.0 g, 3.26 mmol) was dissolved in hot acetone (20 mL). Maleic acid (0.74 g, 6.4 mmol) was dissolved in hot methanol (4 mL) and this solution was then added to the former solution. The combined solutions were left at room temperature overnight but no useful precipitate could be isolated. The mixture was diluted with methanol and the solvent was removed by evaporation. The residue was added to a mixture of toluene (17 mL) and 2-propanol (50 mL). Methanol (20 mL) was added and the mixture was heated until a clear solution was obtained. The solution was cooled to room temperature and then kept in a freezer overnight. A white precipitate was isolated by filtration and then dried at reduced pressure for 48 h. There was obtained 2.4 g of the title compound as a white powder. $^1H$ NMR analysis of the product shows that the sample consists of approximately 1.5 to 2 mol of maleic acid per mol of 1-{1-[(3S)-4-[[3-bromo-5-(trifluoromethyl)benzoyl](methyl)amino]-3-(4-fluorophenyl)butyl]azetidin-3-yl}piperidine-4-carboxamide. $^1H$ NMR (500 MHz, $D_2O$): δ 1.2 (d, 1.6H), 1.8-2.2 (cm, 5.8H), 2.6-2.7 (m, 1H), 2.7 (s, 1H), 2.8-3.2 (cm, 5.1H), 3.2-3.3 (m, 1H), 3.3-3.5 (cm, 2.3H), 3.5-3.8 (m, 1.4H), 3.9-4.1 (m, 0.6H), 4.2-4.7 (cm, 4.6H), 6.3 (s, 2.9H), 6.9-7.3 (m, 4.2H), 7.4 (m, 1H), 8.0 (s, 0.6H).

The maleate salt of 1-{1-[(3S)-4-[[3-Bromo-5-(trifluoromethyl)benzoyl](methyl)amino]-3-(4-fluorophenyl)butyl]azetidin-3-yl}piperidine-4-carboxamide is characterized in providing an X-ray powder diffraction pattern, exhibiting substantially the following main peaks with d-values (d-value: the spacing between successive parallel hkl planes in a crystal lattice):

| Original form of the maleate salt | |
|---|---|
| d-value (Å) | Relative intensity |
| 18.72 | vs |
| 9.49 | vs |
| 9.23 | vs |
| 8.05 | vs |
| 5.72 | vs |
| 5.48 | vs |
| 4.92 | vs |
| 4.77 | vs |
| 4.45 | vs |
| 3.69 | vs |
| 3.42 | vs |
| 3.27 | vs |
| 3.21 | vs |
| 3.19 | vs |

The peaks, identified with d-values calculated from the Bragg formula and intensities, have been extracted from the diffractogram of 1-{1-[(3S)-4-[[3-Bromo-5-(trifluoromethyl)benzoyl](methyl)amino]-3-(4-fluorophenyl)butyl]azetidin-3-yl}piperidine-4-carboxamide maleate. The relative intensities are less reliable and instead of numerical values the following definitions are used:

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with variable slits.

The original form was also obtained following slurrying in water, n-heptane, acetonitrile, isooctane, THF and methyl isobutyl ketone at room temperature.

Form of maleate salt of 1-{1-[(3S)-4-[[3-Bromo-5-(trifluoromethyl)benzoyl](methyl)amino]-3-(4-fluorophenyl)butyl]azetidin-3-yl}piperidine-4-carboxamide following slurrying Samples slurried in methanol, ethanol, i-propanol, aceton and chloroform display very similar patterns in XRPD, which differ from that of the original sample. This form is characterized in providing an X-ray powder diffraction pattern, exhibiting substantially the following main peaks with d-values (d-value: the spacing between successive parallel hkl planes in a crystal lattice):

| Obtained form after suspension in isopropanol | |
|---|---|
| d-value (Å) | Relative intensity |
| 19.1 | s |
| 10.5 | vs |
| 10.3 | s |
| 9.55 | vs |
| 8.09 | vs |
| 7.75 | vs |
| 7.26 | s |
| 6.73 | s |
| 6.36 | s |
| 6.14 | s |
| 5.86 | vs |
| 5.72 | vs |
| 5.41 | s |
| 5.26 | s |
| 5.16 | s |
| 4.94 | vs |
| 4.91 | vs |
| 4.75 | vs |
| 4.49 | vs |
| 4.43 | vs |
| 4.36 | s |
| 4.20 | vs |
| 4.09 | vs |
| 4.05 | vs |
| 3.90 | vs |
| 3.84 | s |
| 3.64 | s |
| 3.58 | vs |
| 3.51 | vs |
| 3.42 | vs |
| 3.35 | vs |
| 3.28 | vs |
| 3.19 | vs |
| 3.11 | s |
| 3.02 | s |
| 2.91 | s |

The peaks, identified with d-values calculated from the Bragg formula and intensities, have been extracted from the diffractogram of the obtained form of 1-{1-[(3S)-4-[[3-Bromo-5-(trifluoromethyl)benzoyl](methyl)amino]-3-(4-fluorophenyl)butyl]azetidin-3-yl}piperidine-4-carboxamide maleate. The relative intensities are less reliable and instead of numerical values the following definitions are used:

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with variable slits.

Form of 1-{1-[(3S)-4-[[3-Bromo-5-(trifluoromethyl)benzoyl](methyl)amino]-3-(4-fluorophenyl)butyl]azetidin-3-yl}piperidine-4-carboxamide maleate following hot-stage XRPD XRPD performed on the sample suspended in i-propanol show that the X-ray powder pattern is changed above 120° C. The new pattern is also different from that of the original sample.

This form is characterized in providing an X-ray powder diffraction pattern, exhibiting substantially the following main peaks with d-values (d-value: the spacing between successive parallel hkl planes in a crystal lattice):

| Obtained form after suspension in isopropanol - increased temp | |
|---|---|
| d-value (Å) | Relative intensity |
| 17.4 | s |
| 10.8 | s |
| 9.65 | s |
| 8.72 | s |
| 7.36 | vs |
| 7.04 | vs |
| 6.58 | vs |
| 4.98 | vs |
| 4.81 | vs |
| 4.76 | vs |
| 4.56 | vs |
| 4.04 | vs |
| 3.65 | vs |
| 3.43 | vs |
| 3.34 | vs |

The peaks, identified with d-values calculated from the Bragg formula and intensities, have been extracted from the diffractogram of the obtained form of 1-{1-[(3S)-4-[[3-Bromo-5-(trifluoromethyl)benzoyl](methyl)amino]-3-(4-fluorophenyl)butyl]azetidin-3-yl}piperidine-4-carboxamide maleate following hot-stage XRPD. The relative intensities are less reliable and instead of numerical values the following definitions are used:

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with variable slits.

Form of 1-{1-[(3S)-4-[[3-Bromo-5-(trifluoromethyl)benzoyl](methyl)amino]-3-(4-fluorophenyl)butyl]azetidin-3-yl}piperidine-4-carboxamide maleate following suspension in methyl ethyl ketone A further form of 1-{1-[(3S)-4-[[3-Bromo-5-(trifluoromethyl)benzoyl](methyl)amino]-3-(4-fluorophenyl)butyl]azetidin-3-yl}piperidine-4-carboxamide was obtained following suspension in methyl ethyl ketone. This form is characterized in providing an X-ray powder diffraction pattern, exhibiting substantially the following main peaks with d-values (d-value: the spacing between successive parallel hkl planes in a crystal lattice):

| Obtained form after suspension in metyl ethyl ketone | |
|---|---|
| d-value (Å) | Relative intensity |
| 10.5 | vs |
| 8.47 | vs |
| 7.49 | vs |
| 6.87 | vs |
| 6.38 | vs |
| 6.20 | vs |
| 5.85 | vs |
| 5.28 | vs |
| 5.16 | vs |
| 4.75 | vs |
| 4.64 | vs |
| 4.49 | vs |
| 4.31 | vs |
| 4.21 | vs |
| 4.10 | vs |
| 3.75 | vs |
| 3.53 | vs |
| 3.33 | vs |
| 3.07 | vs |
| 2.99 | vs |
| 2.89 | vs |

The peaks, identified with d-values calculated from the Bragg formula and intensities, have been extracted from the diffractogram of the obtained form of 1-{1-[(3S)-4-[[3-Bromo-5-(trifluoromethyl)benzoyl](methyl)amino]-3-(4-fluorophenyl)butyl]azetidin-3-yl}piperidine-4-carboxamide maleate following suspension in methyl ethyl ketone. The relative intensities are less reliable and instead of numerical values the following definitions are used:

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with variable slits.

X-Ray Powder Diffractometry (XRPD)

XRPD experiments were performed on a D8 Advance diffractometer (Bruxer AXS GmbH, Karlsruhe, Germany) with Bragg-Brentano geometry, equipped with a VÅNTEC-1 position sensitive detector (PSD). Nickel-filtered Cu $K_\alpha$ radiation was used. The samples, approx. 10 mg, were mounted on a zero-background holder (silicon crystal). Data was collected using continuous scan mode in the range 1-50° 2θ, with a step size of 0.017° and a step time of 0.5 sec. A variable (V20) divergence slit and a detector slit of 12 mm, corresponding to a 3.47° wide detector window, were applied.

Hot-stage XRPD was performed on the instrument described above, using similar settings with an accompanying MRI chamber (Bruxer AXS GmbH, Karlsruhe, Germany), connected to an Ansyco temperature controller.

Example 4

3-Bromo-N-((2S)-2-(4-fluorophenyl)-4-{3-[4-(morpholin-4-ylcarbonyl)piperidin-1-yl]azetidin-1-yl}butyl)-N-methyl-5-(trifluoromethyl)benzamide

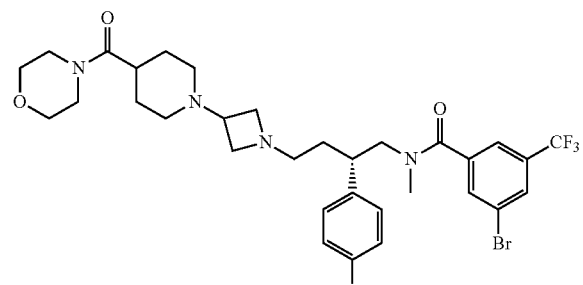

3-Bromo-N-[(2S)-2-(4-fluorophenyl)-4-oxobutyl]-N-methyl-5-(trifluoromethyl)benzamide (see method 1; 0.14 g, 0.31 mmol) and 4-[(1-azetidin-3-ylpiperidin-4-yl)carbonyl]morpholine (see method 5; 0.11 g, 0.42 mmol) were dissolved in methylene chloride (10 mL) together dry methanol (0.2 mL). To the resultant solution were added DIPEA (0.12 g, 0.94 mmol) and sodium triacetoxyborohydride (0.13 g, 0.63 mmol). The mixture was stirred under nitrogen for 4 h at RT. The mixture was diluted with methylene chloride and washed twice with saturated aqueous $NaHCO_3$ and then with brine. The organic phase was filtered through a phase separator and the solvent was removed by evaporation. The product was purified by chromatography on silica gel (methanol-methylene chloride, 10:1). There was obtained 0.11 g (53%) of the title compound as a white foam. $^1$H NMR (500 MHz, $CDCl_3$): δ 1.4-3.8 (cm, 32H), 6.8-7.4 (cm, 6H), 7.7 (s, 1H); LCMS: m/z 684 (M+1)$^+$.

Preparation of Starting Materials

The starting materials for the examples above are either commercially available or are readily prepared by standard methods from known materials. For example, the following reactions are an illustration, but not a limitation, of some of the starting materials.

Method 1

3-Bromo-N-[(2S)-2-(4-fluorophenyl)-4-oxobutyl]-N-methyl-5-(trifluoromethyl)benzamide

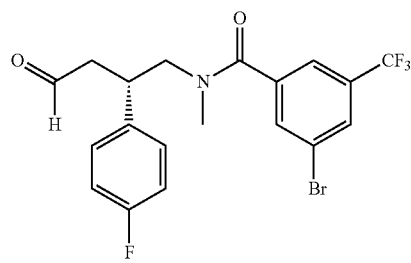

(a) 3-Bromo-N-[(2S)-2-(4-fluorophenyl)pent-4-en-1-yl]-N-methyl-5-(trifluoromethyl)benzamide To a solution of [(2S)-2-(4-fluorophenyl)pent-4-en-1-yl]methylamine (see *Bioorg. Med. Chem. Lett;* 2001; 265-270; 0.54 g, 2.8 mmol) and 3-bromo-5-trifluoromethyl benzoic acid (0.81 g, 3.0 mmol) in DMF (7 mL) were added TBTU (0.96 g, 3.0 mmol) and DIPEA (1.41 g, 10.9 mmol). The reaction mixture was stirred under nitrogen overnight at RT and then partitioned between ethyl acetate and an aqueous NaHCO₃ solution. The aqueous phase was extracted twice with ethyl acetate. The combined organic solutions were washed twice with water and then dried by a phase separator column. The solvent was removed by evaporation and the product was purified by chromatography on silica gel (ethyl acetate-heptane 10% to 17%). There was obtained 0.86 g (68%) of 3-bromo-N-[(2S)-2-(4-fluorophenyl)pent-4-en-1-yl]-N-methyl-5-(trifluoromethyl)benzamide. ¹H NMR (500 MHz, CDCl₃): 2.1-3.8 (cm, 8H), 4.9-5.1 (m, 2H), 5.5-5.8 (m, 1H), 6.8-7.4 (cm, 6H), 7.8 (s, 1H). LCMS: m/z 445 (M+1)+.

(b) 3-Bromo-N-[(2S)-2-(4-fluorophenyl)-4-oxobutyl]-N-methyl-5-(trifluoromethyl)benzamide To a solution of 3-bromo-N-[(2S)-2-(4-fluorophenyl)pent-4-en-1-yl]-N-methyl-5-(trifluoromethyl)benzamide (0.86 g, 1.9 mmol) in acetone (45 mL) were added OsO₄ (2.5% in t-butyl alcohol, 0.49 mL, 0.039 mmol) and 4-methylmorpholine-4-oxide (0.41 g, 3.5 mmol). The solution was stirred under nitrogen at RT overnight and then an aqueous solution of NaHSO₃ (39%, 45 mL) was added. The mixture was stirred for 2 h, diluted with water and then extracted twice with methylene chloride. The combined organic solutions were separated by means of a phase separator column and the solvent was removed by evaporation. The residue (1.08 g) was dissolved in THF (18 mL) and water (4.5 mL) and to the resultant solution was added NaIO₄ (0.73 g, 3.4 mmol). The mixture was stirred under nitrogen overnight at RT. The mixture was partitioned between methylene chloride and water. The aqueous phase was extracted with methylene chloride and then the combined organic solutions were washed with brine and separated by means of a phase separator column. The solvent was removed by evaporation. There was obtained 0.78 g (90%) of the title compound. ¹H NMR (500 MHz, CDCl₃): 2.4-4.4 (cm, 8H), 6.2-8.2 (cm, 7H), 9.8 (s, 1H); LCMS: m/z 447 (M+1)+.

Method 2

1-Azetidin-3-yl-4-(azetidin-1-ylcarbonyl)piperidine

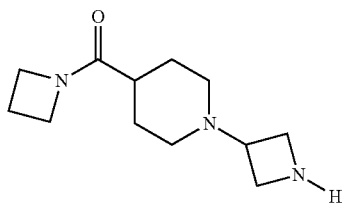

(a) tert-Butyl 4-(azetidin-1-ylcarbonyl)piperidine-1-carboxylate 1-(tert-Butoxycarbonyl)piperidine-4-carboxylic acid (0.40 g, 1.75 mmol) was dissolved in dry DMF (5 mL) and to the solution were added DIPEA (1.22 mL, 7.0 mmol), TBTU (0.67 g, 2.1 mmol) and azetidine (0.12 g, 2.1 mmol). The reaction mixture was stirred at RT for 12 h. The mixture was diluted with methylene chloride and then washed with an aqueous solution of HCl (2 M) and then with an aqueous solution of NaHCO₃ (sat.). The phases were separated by means of a phase separator column and the solvent was removed by evaporation. There was obtained 0.50 g (100%) of tert-butyl 4-(azetidin-1-ylcarbonyl)piperidine-1-carboxylate as a crude solid. ¹H NMR (500 MHz, CDCl₃): 1.4-1.5 (s, 9H), 1.6-1.9 (m, 5H), 2.2-2.4 (m, 3H), 2.6-2.8 (m, 2H), 3.9-4.2 (m, 5H).

(b) 4-(Azetidin-1-ylcarbonyl)piperidine tert-Butyl 4-(azetidin-1-ylcarbonyl)piperidine-1-carboxylate (0.50 g, 1.86 mmol) was dissolved in methylene chloride (10 mL) and to the solution was added trifluoroacetic acid (2.12 g, 18.6 mmol). The mixture was stirred at RT overnight and then the solvent was removed by evaporation. The residue was dissolved in a small amount of methanol and THF and the solution was then loaded on a cation exchange sorbent (Isolute® SCX-2; 10 g). The column washed with THF and the product was then eluted with ammonia saturated methanol. The solvent was removed by evaporation. There was obtained 0.32 g (100%) of 4-(azetidin-1-ylcarbonyl)piperidine. ¹H NMR (500 MHz, CDCl₃): 1.4-1.5 (m, 4H), 2.0-2.2 (m, 3H), 2.4-2.5 (m, 2H), 2.9-3.0 (d, 2H), 3.7-3.8 (t, 2H), 3.9 (s, 1H), 4.0 (t, 2H).

(c) 4-(Azetidin-1-ylcarbonyl)-1-[1-(diphenylmethyl)azetidin-3-yl]piperidine

To a mixture of 4-(azetidin-1-ylcarbonyl)piperidine (0.34 g, 2.0 mmol) and 1-(diphenylmethyl)azetidin-3-one (see *Bioorg. Med. Chem. Lett.;* 13; 2003; 2191-2194, 0.37 g, 1.6 mmol), methanol (5 mL) and acetic acid (0.1 mL) was added (polystyrylmethyl)trimethylammonium cyanoborohydride (4.1 mmol/g, 0.61 g). The reaction mixture was heated for 10 min at 120° C. using microwave single node heating and then filtered through a phase separator. The solvent was removed by evaporation and the product was purified by chromatography on silica gel (methanol-methylene chloride, 5:95). There was obtained 0.42 g (70%) of 4-(azetidin-1-ylcarbonyl)-1-[1-(diphenylmethyl)azetidin-3-yl]piperidine as a colorless foam. ¹H NMR (500 MHz, CDCl₃): 1.6-1.7 (m, 2H), 1.7-1.8 (m, 4H), 2.0-2.1 (m, 1H), 2.2 (qn, 2H), 2.7-2.8 (m, 2H), 2.8-3.0 (m, 3H), 3.4 (t, 2H), 4.0 (t, 2H), 4.1 (t, 2H), 4.4 (s, 1H), 7.1-7.2 (t, 2H), 7.2-7.3 (t, 4H), 7.4 (d, 4H); LCMS: m/z 390 (M+1)+.

(d) 1-Azetidin-3-yl-4-(azetidin-1-ylcarbonyl)piperidine 4-(Azetidin-1-ylcarbonyl)-1-[1-(diphenylmethyl)azetidin-3-yl]piperidine (0.42 g, 1.1 mmol) was dissolved in ethanol and to the resultant solution was added palladium hydroxide on carbon (0.15 g) and ammonium formate (0.28 g, 4.4 mmol). The reaction mixture was heated for 4 min at 120° C. using microwave single node heating. The catalyst was filtered off by means of a phase separator and the filter cake washed with ethanol. The solvent was removed by evaporation and the residue was dissolved in methanol (1 mL) and THF (10 mL). The solution was loaded on a cation exchange sorbent (Isolute® SCX-2; 10 g). The column washed with THF and the product was then eluted with ammonia saturated methanol. The solvent was removed by evaporation and there was obtained 0.25 g of the title compound as colourless oil. ¹H NMR (500 MHz, CD₃OD): 2.0-2.2 (m, 4H), 2.3-2.4 (m, 2H), 2.6-2.8 (m, 3H), 3.2-3.3 (d, 2H), 3.8 (qn, 1H), 4.3 (t, 2H), 4.4 (m, 2H), 4.5 (m, 2H), 4.6 (t, 2H); LCMS: m/z 224 (M+1)+.

Method 3

1-Azetidin-3-yl-N,N-dimethylpiperidine-4-carboxamide

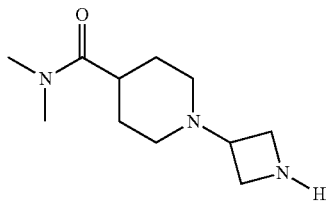

(a) 1-[1-(Diphenylmethyl)azetidin-3-yl]piperidine-4-carboxylic acid

To a mixture of piperidine-4-carboxylic acid (0.13 g, 1.0 mmol) and 1-(diphenylmethyl)azetidin-3-one (see *Bioorg. Med. Chem. Lett.;* 13; 2003; 2191-2194, 0.24 g, 1.0 mmol), methanol (3 mL) and acetic acid (0.3 mL) was added (polystyrylmethyl) trimethylammonium cyanoborohydride (4.1 mmol/g, 0.25 g). The reaction mixture was heated for 5 min at 120° C. using microwave single node heating. Methanol was added and then the resin was filtered off. The solvent was removed by evaporation. There was obtained 0.35 g (100%) of 1-[1-(diphenylmethyl)azetidin-3-yl]piperidine-4-carboxylic acid. $^1$H NMR (500 MHz, CDCl$_3$): 1.6-1.8 (m, 2H), 1.9-2.0 (m, 4H), 2.3-2.4 (m, 1H), 2.7-2.8 (m, 2H), 2.9-3.0 (m, 3H), 3.4 (t, 2H), 4.4 (s, 1H), 7.2 (t, 2H), 7.2-7.3 (t, 4H), 7.4 (d, 4H); LCMS: m/z 351 (M+1)$^+$.

(b) 1-[1-(Diphenylmethyl)azetidin-3-yl]-N,N-dimethylpiperidine-4-carboxamide 1-[1-(Diphenylmethyl)azetidin-3-yl]piperidine-4-carboxylic acid (0.35 g, 0.9 mmol) was dissolved in DMF (8 mL) and to the solution were added TBTU (0.39 g, 1.2 mmol), DIPEA (0.21 mL, 1.2 mmol) and a solution of dimethylamine (3.0 mL, 2M in THF, 6 mmol). The mixture was stirred at RT for 14 h. An aqueous solution of NaHCO$_3$ was added and the mixture was extracted three times with methylene chloride. The combined organic layers were washed with brine and dried over MgSO$_4$. The solvent was removed by evaporation and the product was purified by reversed phase chromatography (C8) using acetonitrile and aqueous ammonium acetate solution (0.1 M) as eluent. There was obtained 0.20 g (59%) of 1-[1-(diphenylmethyl)azetidin-3-yl]-N,N-dimethylpiperidine-4-carboxamide. $^1$H NMR (500 MHz, CDCl$_3$): δ 1.6-2.0 (cm, 6H), 2.4-2.5 (m, 1H), 2.8 (m, 2H), 2.9-3.0 (m, 5H), 3.1 (s, 3H), 3.4 (t, 2H), 4.4 (s, 1H), 7.2 (t, 2H), 7.3 (t, 4H), 7.4 (d, 4H); LCMS: m/z 378 (M+1)$^+$.

(c) 1-Azetidin-3-yl-N,N-dimethylpiperidine-4-carboxamide

Palladium hydroxide on carbon (0.10 g) was placed in a 5 mL vial intended for microwave synthesis. 1-[1-(Diphenylmethyl)azetidin-3-yl]-N,N-dimethylpiperidine-4-carboxamide (0.20 g, 0.53 mmol) dissolved in methanol (3 mL) and acetic acid (0.3 mL) was added. The mixture was stirred under hydrogen (1.6 bar) at RT for four days. The mixture was filtered through a plug of Celite®. The solvent was removed by evaporation and there was obtained 0.11 g (53%) of the title compound.

Method 4

1-Azetidin-3-ylpiperidine-4-carboxamide

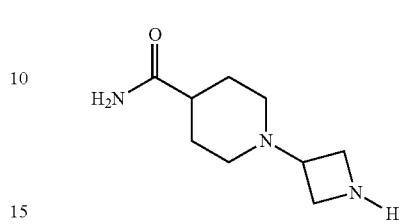

(a) 1-[1-(Diphenylmethyl)azetidin-3-yl]piperidine-4-carboxamide

To a mixture of piperidine-4-carboxamide (1.05 g, 8.2 mmol), 1-(diphenylmethyl)azetidin-3-one (see *Bioorg. Med. Chem. Lett.;* 13; 2003; 2191-2194, 1.94 g, 8.2 mmol), methanol (30 mL) and acetic acid (3 mL) was added (polystyrylmethyl)trimethylammonium cyanoborohydride (4.1 mmol/g, 1.9 g). The reaction mixture was heated for 5 min at 120° C. using microwave single node heating. The resin was filtered off and the solvent was removed by evaporation. There was obtained 2.85 g (99%) of 1-[1-(diphenylmethyl)azetidin-3-yl]piperidine-4-carboxamide. $^1$H NMR (500 MHz, CDCl$_3$): 1.6-1.9 (m, 6H), 2.1-2.2 (m, 1H), 2.7-2.8 (d, 2H), 2.9-3.0 (m, 3H), 3.4 (t, 2H), 4.4 (s, 1H), 5.7-5.8 (b, 1H), 6.2 (b, 1H), 7.2 (t, 2H), 7.2-7.3 (t, 4H), 7.4 (d, 4H); LCMS: m/z 350 (M+1)$^+$.

(b) 1-Azetidin-3-ylpiperidine-4-carboxamide dihydrochloride

1-[1-(Diphenylmethyl)azetidin-3-yl]piperidine-4-carboxamide (1.4 g, 4.1 mmol), ammonium formate (0.77 g, 12 mmol) and ethanol (15 mL) were loaded to a 25 mL vial intended for microwave synthesis. Palladium hydroxide on carbon (0.55 g) was added and the reaction mixture was heated for 2 min at 120° C. using microwave single node heating. The mixture, which still contained starting material, was filtered and to the filtrate was added another portion of palladium hydroxide on carbon together with a mixture of acetic acid and ethanol (1:10). The reaction mixture was stirred under hydrogen (5 bar) at RT for 4 h and then filtered through a plug of Celite®. The solvent was removed by evaporation and the residue was partitioned between toluene and diluted hydrochloric acid. The aqueous phase was freeze-dried and the sticky residue was then co-evaporated with toluene, re-dissolved in water and then freeze-dried. There was obtained 1.35 g (65%) of the title compound. $^1$H NMR (500 MHz, CD$_3$OD): δ 1.6-2.0 (cm, 6H), 2.2-2.3 (m, 1H), 2.8 (m, 2H), 3.4 (m, 1H), 3.9-4.1 (m, 4H).

Method 5

4-[(1-Azetidin-3-ylpiperidin-4-yl)carbonyl]morpholine

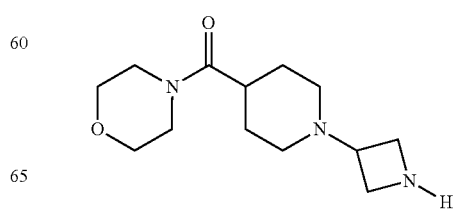

(a) 4-({1-[1-(Diphenylmethyl)azetidin-3-yl]piperidin-4-yl}carbonyl)morpholine 4-(Piperidin-4-ylcarbonyl)morpholine (0.30 g, 1.26 mmol) and 1-(diphenylmethyl)azetidin-3-one (see Bioorg. Med. Chem. Lett.; 13; 2003; 2191-2194, 0.30 g, 1.5 mmol) were dissolved in a mixture of methanol (5 mL) and acetic acid (0.1 mL). (Polystyrylmethyl)trimethylammonium cyanoborohydride (4.1 mmol/g, 0.38 g) was added and the reaction mixture was heated for 10 min at 120° C. using microwave single node heating. The mixture was filtered through a phase separator and the resin washed with methanol. The solvent was removed by evaporation and the residue was dissolved in methylene chloride. The solution washed twice with a saturated solution of $NaHCO_3$. The organic phase was filtered through a phase separator and the solvent was removed by evaporation. The product was purified by chromatography on silica gel (methanol/methylene chloride, 5% methanol). There was obtained 0.44 g (83%) of 4-({1-[1-(diphenylmethyl)azetidin-3-yl]piperidin-4-yl}carbonyl)morpholine as a colorless oil. $^1$H NMR (500 MHz, $CDCl_3$): 1.6-1.7 (m, 2H), 1.7-1.9 (m, 4H), 2.2 (m, 1H), 2.7-2.8 (m, 2H), 2.8-3.0 (m, 4H), 3.3-3.5 (m, 3H), 3.5-3.7 (m, 6H), 4.4 (s, 1H), 7.1-7.2 (t, 2H), 7.2-7.3 (t, 4H), 7.4 (d, 4H); LCMS: m/z 420 $(M+1)^+$.

(b) 4-[(1-Azetidin-3-ylpiperidin-4-yl)carbonyl]morpholine 4-({1-[1-(Diphenylmethyl)azetidin-3-yl]piperidin-4-yl}carbonyl)morpholine (0.44 g, 1.0 mmol) was dissolved in ethanol and to the resultant solution was added palladium hydroxide on carbon (0.15 g) and ammonium formate (0.27 g, 4.2 mmol). The reaction mixture was heated for 2 min at 120° C. using microwave single node heating. The catalyst was filtered off by means of a phase separator and the filter cake washed with ethanol. The solvent was removed by evaporation and the residue was dissolved in methanol (1 mL) and THF (10 mL). The solution was loaded on a cation exchange sorbent (Isolute® SCX-2; 10 g). The column washed with THF and the product was then eluted with ammonia saturated methanol. The solvent of the collected fractions was removed by evaporation and there was obtained 0.11 g of the title compound as colourless oil. $^1$H NMR (500 MHz, $CD_3OD$): 1.7-1.8 (m, 4H), 1.9-2.0 (m, 2H), 2.6-2.9 (m, 4H), 3.3-3.4 (m, 1H), 3.5-3.7 (m, 8H), 3.8-4.0 (m, 3H); LCMS: m/z 254 $(M+1)^+$.

Pharmacology

Transfection and Culturing of Cells Used in FLIPR and Binding Assays

Chinese Hamster Ovary (CHO) K1 cells (obtained from ATCC) were stably transfected with the human $NK_2$ receptor ($hNK_2R$ cDNA in pRc/CMV, Invitrogen) or the human $NK_3$ receptor ($hNK_3R$ in pcDNA 3.1/Hygro (+)/IRES/CD8, Invitrogen vector modified at AstraZeneca EST-Bio UK, Alderley Park). The cells were transfected with the cationic lipid reagent LIPOFECTAMINE™ (Invitrogen) and selection was performed with Geneticin (G418, Invitrogen) at 1 mg/ml for the $hNK_2R$ transfected cells and with Hygromycin (Invitrogen) at 500 μg/ml for the $hNK_3R$ transfected cells. Single cell clones were collected by aid of Fluorescence Activated Cell Sorter (FACS), tested for functionality in a FLIPR assay (see below), expanded in culture and cryopreserved for future use. CHO cells stably transfected with human $NK_1$ receptors originates from AstraZeneca R&D, Wilmington USA. Human $NK_1$ receptor cDNA (obtained from RNA-PCR from lung tissue) was subcloned into pRcCMV (Invitrogen). Transfection was performed by Calcium Phosphate and selection with 1 mg/ml G418.

The CHO cells stably transfected with $hNK_1R$, $hNK_2R$ and $hNK_3R$ were cultured in a humidified incubator under 5% $CO_2$, in Nut Mix F12 (HAM) with Glutamax I, 10% Foetal Bovine Serum (FBS), 1% Penicillin/Streptomycin (PEST) supplemented with 200 μg/ml Geneticin for the $bNK_1R$ and $hNK_2R$ expressing cells and 500 μg/ml Hygromycin for the $hNK_3R$ expressing cells. The cells were grown in T175 flasks and routinely passaged when 70-80% confluent for up to 20-25 passages.

Assessing the Activity of Selected Test Compounds to Inhibit Human $NK_1/NK_2/NK_3$ Receptor Activation (FLIPR Assay)

The activity of a compound of the invention to inhibit $NK_1/NK_2/NK_3$ receptor activation measured as $NK_1/NK_2/NK_3$ receptor mediated increase in intracellular $Ca^{2+}$ was assessed by the following procedure:

CHO cells stably transfected with human $NK_1$, $NK_2$ or $NK_3$ receptors were plated in black walled/clear bottomed 96-well plates (Costar 3904) at $3.5 \times 10^4$ cells per well and grown for approximately 24 h in normal growth media in a 37° C. $CO_2$-incubator.

Before the FLIPR assay the cells of each 96-well plate were loaded with the $Ca^{2+}$ sensitive dye Fluo-3 (TEFLABS 0116) at 4 μM in a loading media consisting of Nut Mix F12 (HAM) with Glutamax I, 22 mM HEPES, 2.5 mM Probenicid (Sigma P-8761) and 0.04% Pluronic F-127 (Sigma P-2443) for 1 h kept dark in a 37° C. $CO_2$-incubator. The cells were then washed three times in assay buffer (Hanks balanced salt solution (HBSS) containing 20 mM HEPES, 2.5 mM Probenicid and 0.1% BSA) using a multi-channel pipette leaving them in 150 μl at the end of the last wash. Serial dilutions of a test compound in assay buffer (final DMSO concentration kept below 1%) were automatically pipetted by FLIPR (Fluorometric Imaging Plate Reader) into each test well and the fluorescence intensity was recorded (excitation 488 nm and emission 530 nm) by the FLIPR CCD camera for a 2 min pre-incubation period. 50 μl of the Substance P ($NK_1$ specific), NKA ($NK_2$ specific), or Pro-7-NKB ($NK_3$ specific) agonist solution (final concentration equivalent to an approximate $EC_{60}$ concentration) was then added by FLIPR into each well already containing 200 μl assay buffer (containing the test compound or vehicle) and the fluorescence was continuously monitored for another 2 min. The response was measured as the peak relative fluorescence after agonist addition and $IC_{50}$s were calculated from ten-point concentration-response curves for each compound. The $IC_{50}$s were then converted to $pK_B$ values with the following formula:

$K_B = IC_{50}/1 + (EC_{60}$ conc. of agonist used in assay/$EC_{50}$ agonist)

$pK_B = -\log K_B$

Determining the Dissociation Constant (Ki) of Compounds for Human $NK_1/NK_2/NK_3$ Receptors (Binding Assay)

Membranes were prepared from CHO cells stably transfected with human $NK_1$, $NK_2$ or $NK_3$ receptors according to the following method.

Cells were detached with Accutase® solution, harvested in PBS containing 5% FBS by centrifugation, washed twice in PBS and resuspended to a concentration of $1\times10^8$ cells/ml in Tris-HCl 50 mM, KCl 300 mM, EDTA-$N_2$ 10 mM pH 7.4 (4° C.). Cell suspensions were homogenized with an UltraTurrax 30 s 12.000 rpm. The homogenates were centrifuged at 38.000×g (4° C.) and the pellet resuspended in Tris-HCl 50 mM pH 7.4. The homogenization was repeated once and the homogenates were incubated on ice for 45 min. The homogenates were again centrifuged as described above and resuspended in Tris-HCl 50 mM pH 7.4. This centrifugation step was repeated 3 times in total. After the last centrifugation step the pellet was resuspended in Tris-HCl 50 mM and homogenized with Dual Potter, 10 strokes to a homogenous solution, an aliquot was removed for protein determination. Membranes were aliquoted and frozen at −80° C. until use.

The radioligand binding assay is performed at room temperature in 96-well microtiter plates (No-binding Surface Plates, Corning 3600) with a final assay volume of 200 μl/well in incubation buffer (50 mM Tris buffer (pH 7.4 RT) containing 0.1% BSA, 40 mg/L Bacitracin, complete EDTA-free protease inhibitor cocktail tablets 20 pills/L (Roche) and 3 mM $MnCl_2$). Competition binding curves were done by adding increasing amounts of the test compound. Test compounds were dissolved and serially diluted in DMSO, final DMSO concentration 1.5% in the assay. 50 μl Non labelled ZD 6021 (a non selective NK-antagonist, 10 μM final conc) was added for measurement of non-specific binding. For total binding, 50 μl of 1.5% DMSO (final conc) in incubation buffer was used. [$^3$H-Sar, Met($O_2$)-Substance P] (4 nM final conc) was used in binding experiments on $hNK_1r$. [$^3$H-SR48968] (3 nM final conc.) for $hNK_2r$ and [$^3$H-SR142801] (3 nM final conc) for binding experiments on $hNK_3r$. 50 μl radioligand, 3 μl test compound diluted in DMSO and 47 μl incubation buffer were mixed with 5-10 μg cell membranes in 100 μl incubation buffer and incubated for 30 min at room temperature on a microplate shaker.

The membranes were then collected by rapid filtration on Filtermat B (Wallac), presoaked in 0.1% BSA and 0.3% Polyethyleneimine (Sigma P-3143), using a Micro 96 Harvester (Skatron Instruments, Norway). Filters were washed by the harvester with ice-cold wash buffer (50 mM Tris-HCl, pH 7.4 at 4° C., containing 3 mM $MnCl_2$) and dried at 50° C. for 30-60 min. Meltilex scintillator sheets were melted on to filters using a Microsealer (Wallac, Finland) and the filters were counted in a β-Liquid Scintillation Counter (1450 Microbeta, Wallac, Finland).

The $K_i$ value for the unlabeled ligand was calculated using the Cheng-Prusoff equation (Biochem. Pharmacol. 22:3099-3108, 1973): where L is the concentration of the radioactive ligand used and $K_d$ is the affinity of the radioactive ligand for the receptor, determined by saturation binding.

Data was fitted to a four-parameter equation using Excel Fit.

$$K_i = IC_{50}/(1+(L/K_d))$$

Results

In general, the compounds of the invention, which were tested, demonstrated statistically significant antagonistic activity at the $NK_1$ receptor within the range of 7-8 for the $pK_B$. For the $NK_2$ receptor the range for the $pK_B$ was 7-9. In general, the antagonistic activity at the $NK_3$ receptor was 7-9 for the $pK_B$.

In general, the compounds of the invention, which were tested, demonstrated statistically significant CYP3A4 inhibition at a low level. The $IC_{50}$ values tested according to Bapiro et al; Drug Metab. Dispos. 29, 30-35 (2001) were generally greater than 10 μM.

Activity Against hERG

The activity of compounds according to formula I against the hERG-encoded potassium channel can be determined according to Kiss L, et al. Assay Drug Dev Technol. 1 (2003), 127-35: "High throughput ion-channel pharmacology: planar-array-based voltage clamp".

In general, the compounds of the invention, which were tested, demonstrated statistically significant hERG activity at a low level. The $IC_{50}$ values tested as described above were generally greater than 8 μM.

Metabolic Stability

The metabolic stability of compounds according to formula I can be determined as described below:

The rate of biotransformation can be measured as either metabolite(s) formation or the rate of disappearance of the parent compound. The experimental design involves incubation of low concentrations of substrate (usually 1.0 μM) with liver microsomes (usually 0.5 mg/ml) and taking out aliquots at varying time points (usually 0, 5, 10, 15, 20, 30, 40 min.). The test compound is usually dissolved in DMSO. The DMSO concentration in the incubation mixture is usually 0.1% or less since more solvent can drastically reduce the activities of some CYP450s. Incubations are done in 100 mM potassium phosphate buffer, pH 7.4 and at 37° C. Acetonitrile or methanol is used to stop the reaction. The parent compound is analysed by HPLC-MS. From the calculated half-life, $t_{1/2}$, the intrinsic clearance, Clint, is estimated by taking microsomal protein concentration and liver weight into account.

In general, the compounds of the invention had in vitro metabolic stability at a high level. Intrinsic clearance values tested as above were generally lower than 25 μl/min/mg protein.

The following table illustrates the properties of the compounds of the present invention:

N-[(2S)-4-{3-[4-(Azetidin-1-ylcarbonyl)piperidin-1-yl]azetidin-1-yl}-2-(4-fluorophenyl)butyl]-3-bromo-N-methyl-5-(trifluoromethyl)benzamide (Ex 1)

| pKB (NK1) | pKB (NK2) | pKB (NK3) | $IC_{50}$ (hERG) | $IC_{50}$ (CYP3A4) | CLint (HLM) |
|---|---|---|---|---|---|
| 7.7 | 8.6 | 8.4 | 11.0 μM | 13.5 μM | 23 μL/min/mg |

Biological Evaluation

Gerbil Foot Tap (NK1 Specific Test Model)

Male Mongolian gerbils (60-80 g) are purchased from Charles River, Germany. On arrival, they are housed in groups of ten, with food and water ad libitum in temperature and humidity-controlled holding rooms. The animals are allowed at least 7 days to acclimatize to the housing conditions before experiments. Each animal is used only once and euthanized immediately after the experiment by heart punctuation or a lethal overdose of pentobarbital sodium.

Gerbils are anaesthetized with isoflurane. Potential CNS-permeable NK1 receptor antagonists are administered intraperitoneally, intravenously or subcutaneously. The compounds are given at various time points (typically 30-120 minutes) prior to stimulation with agonist.

The gerbils are lightly anaesthetized using isoflurane and a small incision is made in the skin over bregma. 10 pmol of ASMSP, a selective NK1 receptor agonist, is administered icv in a volume of 5 µl using a Hamilton syringe with a needle 4 mm long. The wound is clamped shut and the animal is placed in a small plastic cage and allowed to wake up. The cage is placed on a piece of plastic tubing filled with water and connected to a computer via a pressure transducer. The number of hind feet taps is recorded.

Chromodacryorrhea Model (NK1 Specific Test Model)

The actions of antagonists at peripheral NK1 receptors can be assessed in gerbils in vivo using the so-called chromodacryorrhea model (Bristow L J, Young L. Chromodacryorrhea and repetitive hind paw tapping: models of peripheral and central tachykinin NK1 receptor activation in gerbils. Eur J Pharmacol 1994; 253: 245-252). Briefly, systemic (intravenous) administration of NK1 receptor agonists to anaesthetized gerbils results in profuse secretion of red/brown tears in the eyes due to porphyrin secretion from the Harderian gland. NK1 receptor antagonists block NK1-agonist evoked chromodacryorrhea.

Fecal Pellet Output (NK2 Specific Test Model)

The in vivo effect (NK2) of the compounds of formula I can be determined by measuring NK2 receptor agonist-induced fecal pellet output using gerbil as described in e.g. The Journal of Pharmacology and Experimental Therapeutics (2001), pp. 559-564.

Colorectal Distension Model

Colorectal distension (CRD) in gerbils is performed as previously described in rats and mice (Tammpere A, Brusberg M, Axenborg J, Hirsch I, Larsson H, Lindström E. Evaluation of pseudo-affective responses to noxious colorectal distension in rats by manometric recordings. Pain 2005; 116: 220-226; Arvidsson S, Larsson M, Larsson H, Lindström E, Martinez V. Assessment of visceral pain-related pseudo-affective responses to colorectal distension in mice by intracolonic manometric recordings. J Pain 2006; 7: 108-118) with slight modifications. Briefly, gerbils are habituated to Bollmann cages 30-60 min per day for three consecutive days prior to experiments to reduce motion artifacts due to restraint stress. A 2 cm polyethylene balloon (made in-house) with connecting catheter is inserted in the distal colon, 2 cm from the base of the balloon to the anus, during light isoflurane anaesthesia (Forene®, Abbott Scandinavia AB, Solna, Sweden). The catheter is fixed to the tail with tape. The balloons are connected to pressure transducers (P-602, CFM-k33, 100 mmHg, Bronkhorst HI-TEC, Veenendal, The Netherlands). Gerbils are allowed to recover from sedation in the Bollmann cages for at least 15 min before the start of experiments.

A customized barostat (AstraZeneca, Mölndal, Sweden) is used to manage air inflation and balloon pressure control. A customized computer software (PharmLab on-line 4.0) running on a standard computer is used to control the barostat and to perform data collection. The distension paradigm used consists of 12 repeated phasic distensions at 80 mmHg, with a pulse duration of 30 sec at 5 min intervals. Compounds or their respective vehicle are administered as intraperitoneal (i.p.) injections before the CRD paradigm. Each gerbil receives both vehicle and compound on different occasions with at least two days between experiments. Hence, each gerbil serves as its own vehicle control.

The analog input channels are sampled with individual sampling rates, and digital filtering is performed on the signals. The balloon pressure signals are sampled at 50 samples/s. A highpass filter at 1 Hz is used to separate the contraction-induced pressure changes from the slow varying pressure generated by the barostat. A resistance in the airflow between the pressure generator and the pressure transducer further enhances the pressure variations induced by abdominal contractions of the animal. A customized computer software (PharmLab off-line 4.0) is used to quantify the magnitude of highpass-filtered balloon pressure signals. The average rectified value (ARV) of the highpass-filtered balloon pressure signals is calculated for 30 s before the pulse (i.e. baseline response) and for the duration of the pulse. When calculating the magnitude of the highpass-filtered balloon pressure signals, the first and last seconds of each pulse are excluded since these reflect artifact signals produced by the barostat during inflation and deflation and do not originate from the animal.

The invention claimed is:

1. A compound having the formula:

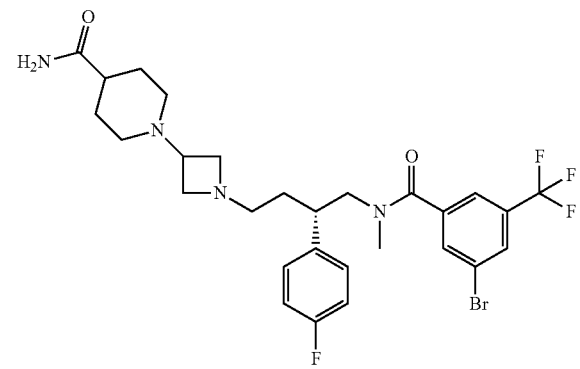

or a pharmaceutically and pharmacologically acceptable salt thereof.

2. A pharmaceutical formulation comprising a compound according to claim 1 and a pharmaceutically acceptable carrier or diluent.

3. A method for antagonizing tackykinin action at the NK (neurokinin) receptors in a patient, which comprises administering to the patient a therapeutically effective amount of a compound according to claim 1.

* * * * *

UNITED STATES PATENT AND TRADEMARK OFFICE
CERTIFICATE OF CORRECTION

PATENT NO. : 8,106,208 B2 Page 1 of 1
APPLICATION NO. : 11/747322
DATED : January 31, 2012
INVENTOR(S) : Anders Johansson It is certified that error appears in the above-identified patent and that said Letters Patent is hereby corrected as shown below:

Column 24, Line 55 (Claim 3), please delete "tackykinin" and insert --tachykinin--, therefor.

Signed and Sealed this
Fifteenth Day of May, 2012

David J. Kappos
*Director of the United States Patent and Trademark Office*